United States Patent
Attstrom et al.

(10) Patent No.: US 10,206,928 B2
(45) Date of Patent: Feb. 19, 2019

(54) METHOD OF MAINTAINING ORAL HEALTH IN ANIMALS

(71) Applicant: MERIAL INC., Duluth, GA (US)

(72) Inventors: Rolf Valter Attstrom, Brienz (CH); Hugo De Bruyn, Lennik (BE)

(73) Assignee: Merial Inc., Duluth, GA (US)

( * ) Notice: Subject to any disclaimer, the term of this patent is extended or adjusted under 35 U.S.C. 154(b) by 0 days.

(21) Appl. No.: 15/801,109

(22) Filed: Nov. 1, 2017

(65) Prior Publication Data
US 2018/0064719 A1 Mar. 8, 2018

Related U.S. Application Data

(63) Continuation of application No. 12/162,168, filed as application No. PCT/GB2007/000680 on Feb. 27, 2007.

(30) Foreign Application Priority Data

Feb. 28, 2006 (GB) .................................. 0604018.2

(51) Int. Cl.
*A61K 31/5377* (2006.01)
*A61K 8/49* (2006.01)
*A61Q 11/00* (2006.01)

(52) U.S. Cl.
CPC ............ *A61K 31/5377* (2013.01); *A61K 8/49* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 4,636,382 A | 1/1987 | Hernestam | |
| 4,894,221 A | 1/1990 | Hernestam et al. | |
| 4,975,270 A | 12/1990 | Kehoe | |
| 5,015,485 A | 5/1991 | Scaglione et al. | |
| 5,082,653 A | 1/1992 | Pan et al. | |
| 5,085,850 A | 2/1992 | Pan et al. | |
| 5,329,881 A | 7/1994 | O'Rourke | |
| 5,467,741 A | 11/1995 | O'Rourke | |
| 6,309,676 B1 | 10/2001 | Lewandowski | |
| 2001/0043941 A1 | 11/2001 | Huatan et al. | |
| 2001/0053375 A1 | 12/2001 | Sagel et al. | |
| 2003/0103914 A1 | 6/2003 | Lawlor | |
| 2004/0115247 A1 | 6/2004 | Melman | |
| 2004/0156884 A1 | 8/2004 | Brown et al. | |
| 2005/0095208 A1 | 5/2005 | Battaglia et al. | |
| 2005/0158252 A1 | 7/2005 | Romanowski et al. | |

FOREIGN PATENT DOCUMENTS

| | | |
|---|---|---|
| EP | 1 136 067 | 9/2001 |
| WO | WO 90/14342 | 11/1990 |
| WO | WO 02/02128 | 1/2002 |
| WO | WO 2006/105196 | 10/2006 |
| WO | WO 2006/128270 | 12/2006 |

OTHER PUBLICATIONS

A.G. Al-Bakri et al, "The assessment of the antibacterial and antifungal activities of aspirin, EDTA and aspirin-EDTA combination and their effectiveness as antibiofilm agents", Journal of Applied Microbiology, (Jul. 1, 2009), vol. 107, No. 1, doi:10.1111/j.1365-2672.2009.04205.x, ISSN 1364-5072, pp. 280-286, XP055037397.

Brown Wendy Y et al, "Effective periodontal disease control using dental hygiene chews", Journal of Veterinary Dentistry, American Veterinary Dental Society, Lockport, US, (Mar. 1, 2005), vol. 22, No. 1, ISSN 0898-7564, pp. 16-19, XP008170620.

Collaert et al., "Microbiology of early supragingival plaque development after delmopinol treatment", Oral Microbiology and Immunology, Feb. 1993, vol. 8, No. 1, pp. 36-41.

Daniel Ravel, DDS (Pediatric Dental Health: Halitosis and Bad Breath in Children (Apr. 1, 2003); http://dentalresource.org/topic48halitosis.htm).

Decapinol® (Sinclair. www.decapinol.com).

Dr. Joan I. Gluch, ROH, PhD ("Sugar Free Chewing Gums and Caries Prevention", Contemporary Oral Hygiene. Oct. 2003: p. 1).

(Continued)

*Primary Examiner* — Samantha L Shterengarts
(74) *Attorney, Agent, or Firm* — Judy Jarecki-Black; Katrina Bergbauer; Merial Inc.

(57) ABSTRACT

Use of a compound having the formula (I) in a medicament for the prevention or treatment of a disease caused by oral bacteria in an animal wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, or a pharmaceutically acceptable salt thereof.

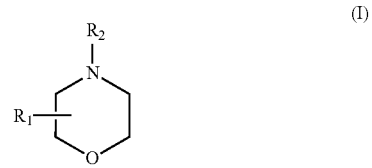

(I)

9 Claims, No Drawings

(56) References Cited

OTHER PUBLICATIONS

Edwardsson C B et al, "Microbiology of Early Supragingival Plaque Development After Delmopinol Treatment", Oral Microbiology and Immunology, Munksgaard, Copenhagen, DK, (Jan. 1, 1993), vol. 8, No. 1, ISSN 0902-0055, pp. 36-41, XP008067768.
Elworthy et al., "Antimicrobial properties of delmopinol against oral bacteria." Letters in Applied Microbiology, 1995, vol. 20, No. 3, pp. 191-194.
FDA submission extract by the Applicant for regulatory approval of a commercial formulation of delmopinol. Submitted to the EPO during prosecution of EP 07700329.1.
Hase et al. (Journal of Clinical Periodontology; vol. 25, Issue 9, pp. 746-753, Sep. 1998).
ISR for PCT/GB2007/000025.
ISR for PCT/GB2007/000680.
Mariana A. Montenegro et al. (2012). Gum Arabic: More Than an Edible Emulsifier, Products and Applications of Biopolymers, Dr. Johan Verbeek (Ed.), ISBN: 978-953-51-0226-7.
Quirynen et al., "The impact of periodontal therapy and the adjunctive effect of antiseptics on breath odor related outcome variables: a double-blind randomized study", Journal of Periodontology, May 2005, vol. 76, No. 5, pp. 705-712.
Rundegren et al., "Delmopinol interactions with cell walls of gram-negative and gram-positive oral bacteria," Oral Microbiology and Immunology, 1995, vol. 10, pp. 102-109.

METHOD OF MAINTAINING ORAL HEALTH IN ANIMALS

CROSS-REFERENCE TO RELATED APPLICATIONS

This application is a continuation of, and claims benefit of, U.S. patent application Ser. No. 12/162,168, filed on Jan. 17, 2011, which is a National Stage Application of PCT/GB2007/000680, filed on Feb. 27, 2007, which claims priority to Great Britain Application No. 0604018.2, filed on Feb. 28, 2006, which are incorporated herein in their entirety.

FIELD OF THE INVENTION

The present invention relates to the maintenance of oral health in animals.

BACKGROUND TO THE INVENTION

The need to maintain good oral health in humans has been recognised for a very long time. However, it is only recently that significant advances in maintaining the oral health of animals have been made. In particular, there has been a rapid increase in the number of academic publications in the field of veterinary dentistry in the last 20 years; the Academy of Veterinary Dentistry and the American Veterinary Dental College were established in 1987 (Easley, J Hist Dent: Vol. 47, No. 2. Jul. 1999 pp 83-85).

Veterinary oral health products and treatments are a rapidly growing multi-million pound industry, in particular in the pet, or "companion animal", sector. US retail sales in this sector are estimated to be greater than US$400 m per year.

Animals are susceptible to the majority, if not all, of the adverse oral health conditions that affect humans, including the formation of plaque and tartar (calculus), gingivitis, periodontitis, unsightly dental staining and halitosis. Methods and products are required to prevent and treat all of these conditions. It is particularly important to maintain oral health in animals because the range of corrective measures that are available to humans, such as dentures and complex dental surgery, are not readily available for animals.

Delmopinol is a morpholino compound that has utility in the removal or inhibition of dental plaque in humans. The compound and its manufacture are disclosed in U.S. Pat. No. 4,894,221.

SUMMARY OF THE INVENTION

The present invention is based on the surprising finding that a composition comprising Delmopinol (or a derivative or salt thereof) is effective in maintaining the oral health of animals, in particular companion animals.

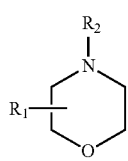
(I)

According to a first aspect of the invention, a compound having the formula (I) is used in the manufacture of a medicament for the prevention or treatment of a disease caused by oral bacteria in an animal, wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, or a pharmaceutically acceptable salt thereof.

According to a second aspect of the invention, a cosmetic method of preventing or decreasing oral staining in an animal comprises the step of exposing the oral cavity to a morpholino compound of general formula (I).

According to a third aspect of the invention, an animal chew comprises a compound of formula (I) or a medicament comprising the compound of formula (I).

According to a fourth aspect of the invention, an animal foodstuff comprises a compound of formula (I).

DETAILED DESCRIPTION OF THE INVENTION

A morpholino compound of formula (I) is effective in maintaining the health and favourable aesthetics of an animal's oral cavity. A morpholino compound according to the invention has the general formula (I)

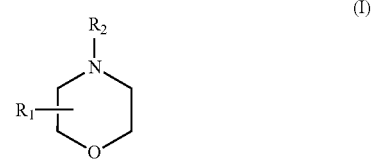
(I)

wherein $R_1$ is a straight or branched alkyl group containing 8 to 16 carbon atoms at the 2- or 3- position of the morpholino ring, and $R_2$ is a straight or branched alkyl group containing 2 to 10 carbon atoms, substituted with a hydroxy group except in the alpha-position, or pharmaceutically acceptable salts thereof. In a preferred embodiment, the sum of the carbon atoms in the groups $R_1$ and $R_2$ of the morpholino compound is at least 10, preferably between 10 and 20. In a further preferred embodiment, the $R_2$ group terminates with the hydroxy group.

The claimed morpholino compounds are known per se and can be manufactured by any known method, for example that disclosed in U.S. Pat. No. 5,082,653 and WO90/14342, which are incorporated herein by reference.

The preferred morpholino compound for use in the invention is 3-(4-propyl-heptyl)-4-(2-hydroxyethyl)morpholine, which is commonly known as Delmopinol (CAS No. 79874-76-3).

The morpholino compounds can be used in their free base form or as a pharmaceutically acceptable salt thereof. Examples of pharmaceutically acceptable salts are the salts of acids such as acetic acid, phosphoric acid, boric acid, hydrochloric acid, maleic acid, benzoic acid, citric acid, malic acid, oxalic acid, tartaric acid, succinic acid, glutaric acid, gentisic acid, valeric acid, gallic acid, beta-resorcyclic acid, acetyl salicylic acid, salicylic acid, perchloric acid, barbituric acid, sulfanilic acid, phytic acid, p-nitro benzoic acid, stearic acid, palmitic acid, oleic acid, myristic acid, lauric acid and the like. The most preferred salts are those of hydrochloric acid. A preferred compound is delmopinol hydrochloride (CAS No. 98092-92-3).

The morpholino compounds are useful in preventing and treating diseases caused by oral bacteria in an "animal". As used herein, the term "animal" is to be given its recognised meaning in the art, i.e. any non-human member of the animal kingdom. Preferably, the animal is a non-human mammal.

In a preferred embodiment, the animal is a "companion animal". As used herein, the term "companion animal" refers to an animal that is kept as a "pet" by a person for companionship and enjoyment. These will usually be mammals such as cats, dogs, rabbits, ferrets and rodents. The most preferred companion animals are cats and dogs.

In an alternative embodiment, the animal is "livestock", i.e. an animal that is reared agriculturally to provide a useful product. A livestock animal is usually a mammal, including but not limited to pigs, cows, goats, donkeys, sheep and llamas.

In another alternative embodiment, the animal is a "performance animal" such as a racehorse or racing greyhound. The skilled person will recognise the need for these animals to be maintained in optimum health, including oral health.

The morpholino compounds have been found to be particularly effective in maintaining the health and favourable aesthetics of an animal's oral cavity. The morpholino compounds have several medical (i.e. veterinary) applications, as follows: prevent and remove plaque and calculus formation in the oral cavity, particularly on the teeth; prevent and treat gum diseases including gingivitis and periodontitis; and prevent and treat halitosis. They also have a cosmetic application, as they are able to remove stains from, or "whiten", the teeth.

A morpholino compound of formula (I) may be incorporated into a medicament, composition or formulation. When a morpholino compound according to the invention is manufactured as a medicament, the skilled person will realise that the morpholino compound of formula (I) may be the only active ingredient in the final medicament. However, the final medicament may contain other pharmaceutically acceptable ingredients, both inert (i.e. an "excipient") and pharmaceutically active. Any combination of a compound of formula (I) and one or more of the pharmaceutically acceptable ingredients disclosed below is within the scope of the invention. When the compound of formula (I) is prepared as a cosmetic, excipients may be added, which will be apparent to one skilled in the art.

The compound of formula (I) may be administered to an animal in combination with at least one anti-microbial, preferably anti-bacterial, agent. Suitable agents include the antibiotics tetracycline, doxycycline and ampicillin and the anti-bacterial agents triclosan (2,4,4'-trichloro 2'-hydroxy diphenyl ether) and Chlorhexidine digluconate (1,1'-hexamethylene-bis[(5-p-clorophenyl)-biguanide]).

The compound of formula (I) is useful in treating and preventing gum disease and associated inflammation of the gums. The compound of formula (I) may be administered to an animal in combination with at least one anti-inflammatory agent. Anti-inflammatory agents are well known in the art and any may be used. Preferably, the anti-inflammatory agent is a non-steroidal anti-inflammatory drug (NSAID), such as aspirin (acetylsalicylic acid) or ibuprofen. In an alternative embodiment, a steroidal anti-inflammatory agent, for example cortisone, may be used.

The compound of formula (I) can be added to toothpaste, dentifrice, gum, gel or mouthwash formulations. The concentration of the morpholino compound of formula (I) that is required will vary depending on the animal to be treated and the nature of the formation, as will be apparent to the skilled person. An example of a suitable concentration of the preferred compound, delmopinol, is 0.2% w/v.

In a preferred embodiment, the compound is present in an animal chew. As used herein, the term "chew" is given its normal meaning in the art and refers to any toy, accessory or foodstuff that is intended for chewing or gnawing by an animal. The skilled person will recognise that suitable "chew" size and composition will vary depending on the animal. Chews may be made from animal products such as hide (animal skin), tendon or bone, man-made products such as plastics (e.g. nylon) and man-made rubber, and plant products such as natural rubber. Other suitable materials for making a chew will be apparent to the skilled person. A combination of materials may be used. Preferably, the chew provides sufficient resistance to the chewing action of an animal that pressure is put on the animal's teeth. It also acts to remove debris, plaque and/or calculus by friction.

The chew may be in any shape, for example, a chew made for a cat may be in the shape of a mouse and a chew for a dog may be in the shape of a bone. Preferably, the chew is shaped so that the teeth, gums and tongue are rubbed or massaged by the chew as the animal chews it, for example the chew may have a surface containing bumps, nodules or ridges. This will aid plaque removal.

In a preferred embodiment, a compound of formula (I) is infused into the chew, i.e. the chew material contains the compound of formula (I) and releases it over a sustained period. An example of a method of infusing a chew is to soak hide in a compound of formula (I) and then allow it to dry. In an alternative embodiment, the chew is simply coated with a compound of formula (I). The chew may be flavoured with a flavouring that is appealing to the animal it is designed for. As an example, a dog chew may be flavoured with meat flavours, such as chicken or beef.

The compound of formula (I) may alternatively be incorporated into a foodstuff that does not resist the chewing or gnawing action of an animal, i.e. foodstuffs that are readily broken down by the chewing or gnawing action. Preferred examples of such foodstuffs include animal feeds (both wet and dry), more preferably animal biscuits. The compound of formula (I) can be incorporated into, or coated onto the surface of, such foodstuffs. The compound of formula (I) could also be added to the animal's usual feed.

The chew or foodstuff comprising a compound of formula (I) can additionally comprise any of the other medicament ingredients disclosed herein, in any combination. For example, an animal foodstuff or chew can contain a compound of formula (I) and one or more active or inert pharmaceutical ingredients, such as an antimicrobial agent or an anti-inflammatory agent.

A single type of morpholino compound, or a number of different compounds may be present in the composition, medicament or formulation. When a number of compounds are present, it is preferred that delmopinol is the major morpholino compound.

In one embodiment, a compound of formula (I) is used to remove or prevent plaque formation in the oral cavity, preferably the teeth and gums, of an animal. Prevention of plaque formation will prevent the formation of tartar (calculus), which forms when plaque calcifies and hardens. The terms "plaque" and "calculus" are given their normal meaning in the art. For the avoidance of doubt, plaque is a bacteria-based film that can occur on oral surfaces. Calculus (also known as tartar) is a hardened deposit that can form when plaque is not removed. The two major forms of gum disease, gingivitis and periodontitis, result from bacterial plaque formation in the oral cavity, in particular on the teeth and gums. Although long considered to be a localised infection only, gum disease is now being investigated as a potential risk factor for the development of other, potentially more serious, diseases including cardiovascular disease and pulmonary disorders. Therefore, compounds of the formula (I) can be used to treat (by removing plaque) and prevent (by preventing plaque formation) gum diseases such as gingivitis and periodontitis. In a preferred embodiment, the gum disease has symptoms including infected sub-gingival pockets. More preferably, the infected sub-gingival pockets are at least 4 mm deep, measured from the tip of the gum line to the apex of the pocket.

A morpholino compound of formula (I) can be used to treat and prevent halitosis. As used herein, the term "halitosis" refers to the commonly recognised meaning of the term, i.e. "bad breath". This may be defined as breath that has an odour that is unpleasant or offensive to the animal exhaling the breath, or more likely to people near the animal such as the owner. In a preferred embodiment, the breath contains Volatile Sulphur Compounds (VSC's), including but not limited to hydrogen sulphide, methyl mercaptan or dimethylsuphide, or compounds such as putrescine, cadaverine, butyric and propionic acids. These compounds result from proteolytic degradation of various sulphur-containing substrates in food debris, saliva, blood and epithelial cells, by predominantly anaerobic Gram-negative microorganisms in the oral cavity. A compound of formula (I) can reduce the level of these compounds emitted from an animal's mouth.

A composition comprising a compound of formula (I) can be used purely cosmetically, to reduce and prevent staining in the oral cavity. In particular, a compound of formula (I) can whiten the teeth. Any combination of a compound of formula (I) and one or more excipients, as described herein, is within the scope of this embodiment.

As used herein, the term "oral staining" refers to any unsightly discolouration of the oral cavity. In particular, it refers to staining of the teeth and tongue. The staining that is prevented and/or removed by a compound of formula (I) is caused by staining agents affecting the surfaces of the oral cavity, preferably the surface of the tongue and teeth, most preferably the surfaces of the teeth that are visible to others. This is commonly referred to as "extrinsic staining".

The staining can be caused by any staining agent. Animal feed can cause dental staining, referred to herein as "dietary" staining agents. The anti-bacterial agent Chlorhexidine, which is used to treat oral infections in animals, also causes staining of the teeth. Compounds of the formula (I) can remove stains caused by these agents (amongst others), and prevent further staining.

It should be understood that the term "oral staining" includes staining of teeth, i.e. dental staining. The compound of formula (I) can therefore be used to prevent and remove dental staining. The removal of (dark) stains from the teeth, to give them a "whiter" appearance, is referred to herein as "whitening" of the teeth. In a preferred embodiment, the compound of formula (I) is added simultaneously or sequentially with an additional de-staining agent. This additional agent preferably comprises a peroxide-containing whitener or bleaching agent. The combination of a compound of formula (I) and another agent that is known to remove/prevent staining demonstrates a surprising synergy that allows stains to be removed, i.e. teeth to be whitened, more effectively than when each of the agents is used separately. Alternatively, the compound of formula (I) is the only active de-staining ingredient in the preparation with which the oral cavity is contacted.

For all embodiments described herein, the oral cavity is exposed to (i.e. brought into contact with) a compound of formula (I). The compound of formula (I) is brought into contact with the oral cavity in a conventional way, in any suitable form or amount that achieves the desired effect in the oral cavity, i.e. the reduction or prevention of plaque formation, prevention or treatment of gum diseases including gingivitis and periodontitis including treatment of infected sub-gingival pockets; prevention or treatment of halitosis or teeth whitening.

Preferably, the compound of formula (I) is in the form of an aqueous mouthwash, toothpaste, gel, gum, dentifrice or other similar preparation that will be apparent to the skilled person. In an equally preferable embodiment, the compound of formula (I) contacts the oral cavity via its presence on or in a chew or foodstuff, as detailed above. Preferably, the compound, in whichever form is suitable, is held in the mouth for at least 5 seconds, preferably greater than 10 seconds, for example one minute or more. In a preferred embodiment, mechanical agitation, preferably brushing or scraping the teeth, tongue or gums, is performed simultaneously with or shortly, preferably immediately, after contacting the oral cavity with a compound of formula (I). However, mechanical agitation is not required for the compounds of formula (I) to be effective in maintaining the health and favorable aesthetics of an animal's oral cavity. Simple contact of the oral cavity with a compound of formula (I) is sufficient for the benefits described herein to be obtained. In one embodiment, the compound of formula (I) is applied as an aqueous mouthwash at the start of any regular (e.g. daily) oral health routine, such as before brushing the teeth. In a preferred embodiment, the mouthwash is applied as a spray or mist, for example an aerosol spray, or as droplets from a dropper bottle. In a further preferred embodiment, the oral cavity is contacted with a compound of formula (I) shortly, preferably immediately, before contacting the oral cavity with a further agent that is helpful in maintaining good oral conditions, for example a further de-staining agent, as described above.

A method for treating (veterinary or cosmetically) any of the oral health conditions disclosed herein comprises contacting the oral cavity of an animal that displays symptoms of one or more of the conditions with a compound of formula (I), preferably a preparation, composition or formulation containing a compound of formula (I) such as a toothpaste, gum, gel, dentifrice, mouthwash formulation, chew or foodstuff. Halitosis, plaque formation, calculus and gum disease can be prevented by contacting the oral cavity with a compound of formula (I), preferably a preparation containing a compound of formula (I) such as a toothpaste, gum, gel, mouthwash formulation, chew or foodstuff, prior to the development of offensive odours, plaque, calculus or disease.

The invention is further described by the following non-limiting example.

EXAMPLE

A study was carried out to investigate the effect of dog snacks containing delmopinol on gingivitis and calculus formation in beagle dogs.

Materials and Methods

Eight female dogs were used in the study. The animals were two years old and each weighed approximately 20 kilos. The dogs were divided randomly into two groups of four. The experimental group received a daily dog snack containing delmopinol, while the control group received a daily dog snack without delmopinol.

During a pre-experimental period of four weeks, the teeth in the upper jaws of all dogs were scaled and polished professionally with a rubber cup, pumice and water, on a weekly basis. The teeth of the upper jaws were also thoroughly brushed with a toothbrush and water, for 2 minutes daily. The teeth in the lower jaws were not cleaned. During this pre-experimental period the dogs were fed a soft gingivitis-inducing diet. Using these procedures, two different clinical conditions prevailed in the dogs at the end of the pre-experimental period: in the upper jaw the gingiva was clinically healthy while in the lower jaws gingivitis prevailed.

Commercially available dog snacks (pieces of cow/pig hides approximately 12-15 cm long and with a diameter of around 1.5 cm) were soaked in delmopinol 10 mg/ml overnight and then dried. The experimental dogs received a portion of the delmopinol dog snack daily in the afternoon from day 0 until day 14 of the experimental period. The control dogs received an equal amount of dog snack without delmopinol during the corresponding period. Between days 0 to 28 of the experiment the dogs were fed a soft plaque and calculus-promoting diet only.

Measurements

In the upper jaws, the presence of plaque and gingivitis was measured at the buccal surfaces of canines, first, second, third, fourth premolars and first molars. In the lower jaws the measurements were undertaken at the buccal surfaces of canines and first molars. In total 16 surfaces were examined clinically. 12 surfaces were clinically healthy prior to the experimental period and 4 surfaces were not maintained with oral hygiene measures.

All experimental procedures, (except the tooth brushing during the pre-experimental period) were performed with the dogs anaesthetized by intravenous Pentothal (Abbot, Belgium).

The experimental procedures and measurements were blinded and the examiner did not know which group the animals belonged to. The various measurements were taken on days 0, 14 and 28. Clinical photos were taken of the upper jaws at the same occasions as the measurements.

Parameters

The presence of plaque was scored following staining of the teeth with erythrosine dye. Plaque was noted if stained dental plaque was in contact with the buccal gingival margin.

Bleeding on probing was scored according to Löe, H and Silness, J (1963) Periodontal disease in pregnancy. Prevalence and severity. Acta Odontologica Scandinavica 21, 533-551. Presence of gingivitis was registered if bleeding occurred within 20 seconds following gentle probing of the buccal gingival margin.

Presence or absence of calculus was noted on the buccal surfaces of the teeth in the upper jaws.

Results

The delmopinol-containing dog snack was well tolerated by the dogs. No remains of the dog snacks were found in the dog cages showing that the dogs had consumed all the dog snacks provided.

Dental Plaque

On day 0 the teeth in the upper jaws of all dogs were plaque free due to the polishing of the teeth. On day 14 all teeth in the control group harboured dental plaque while the experimental group showed a reduction of around 20% in the presence of dental plaque relative the control dogs. On day 28 all teeth in both groups demonstrated dental plaque (see Table 1).

Bleeding on Probing

On day 0 only one site in each of the experimental and control groups showed bleeding on probing in the previously well-maintained (healthy) maxillary (upper jaw) quadrants. On day 14, 13 of the 48 measured maxillary teeth/gingival units in the experimental group had bleeding on probing while the corresponding value for the control group was 36/48.

In the experimental dogs, 15 of the 16 sites at the previously not maintained lower jaw teeth demonstrated bleeding on probing on day 0. On day 14 the bleeding at these teeth was reduced to five sites. On day 28 bleeding on probing had increased to 21/48 sites at the upper jaw teeth and to 12/16 at the lower jaw teeth. In the control group, one site in the upper jaw and all 16 sites at the lower jaw teeth on day 0 showed bleeding on probing. On day 14 in the control group 36/48 sites in the upper jaw had bleeding on probing while at the lower jaw teeth the bleeding on probing was reduced to 8. On day 28 bleeding on probing had increased to 26/48 sites at the upper jaw teeth and to 14/16 sites at the lower jaw teeth (see Table 2).

Calculus Formation

None of the of the teeth in the experimental and control group had calculus on day 0 because prior to the experimental start all calculus was professionally removed. On day 14 in total 6/48 maxillary (upper jaw) sites in the experimental group had calculus while the corresponding value in the control group was 35 sites. On day 28 the number of sites with calculus was 37/48 in the experimental group and 40/48 in the control group (see Table 3).

Conclusions

Adding delmopinol to the tested dog snacks proved to be effective in all dogs. Chewing on the snack alone reduces established gingivitis by 50% but when delmopinol was added in the snack, the reduction was 69% even in the presence of measurable plaque accumulation.

When the pre-experimental oral hygiene measures were stopped, a rapid plaque formation is seen. Within 2 weeks all surfaces exhibit plaque. The use of the snacks, with or without the tested component, did not alter plaque accumulation. However, the bleeding (which is an indication of the continuous plaque activity) was reduced. Without wishing to be bound by theory, delmopinol appears to reduce plaque maturation in such a way that the plaque that is present stays immature and does not provoke the inflammatory response that normally leads to gingivitis. Although the inflammation increased in all dogs after stopping the pre-experimental oral hygiene routine, it was significantly less (paired t-test $p=0.05$) in the experimental group.

The most prominent effect of the delmopinol dog chew in this study was seen on calculus formation. Even in the presence of dental plaque and with a calculus-promoting soft diet, the calculus formation was strongly reduced in the experimental group. This indicates that the plaque is loosely bound and less densely packed on the tooth surface, which has an effect on the mineralisation of deposits. When the application of delmopinol was stopped, a rapid re-growth of calculus was measurable in all experimental animals, although the measurable visible plaque accumulation was unaltered.

This study indicates that administration of delmopinol in a dog snack retards gingivitis formation, reduces established inflammation and inhibits calculus formation.

TABLE 1

Number of sites with presence of dental plaque on the buccal surfaces of the upper teeth (n = 48) (UJ) and on teeth in the lower jaw (n = 16) (LJ) during the experimental period of 28 days.

| Dog | Day 0 UJ | Day 0 LJ | Day 14 UJ | Day 14 LJ | Day 28 UJ | Day 28 LJ |
|---|---|---|---|---|---|---|
| Delmopinol | | | | | | |
| 1 | 0 | 4 | 8 | 4 | 12 | 4 |
| 2 | 0 | 4 | 12 | 4 | 12 | 4 |
| 3 | 0 | 4 | 12 | 4 | 12 | 4 |
| 4 | 0 | 4 | 6 | 4 | 12 | 4 |
| Sum | 0 | 16 | 38 | 16 | 48 | 16 |
| Control | | | | | | |
| 1 | 0 | 4 | 12 | 4 | 12 | 4 |
| 2 | 0 | 4 | 12 | 4 | 12 | 4 |
| 3 | 0 | 4 | 12 | 4 | 12 | 4 |
| 4 | 0 | 4 | 12 | 4 | 12 | 4 |
| Sum | 0 | 16 | 48 | 16 | 48 | 16 |

TABLE 2

Number of sites with gingival bleeding at the buccal surfaces of the upper teeth (n = 48) (UJ) and at teeth in the lower jaw (LJ) (n = 16) during the experimental period of 28 days.

| Dog | Day 0 UJ | Day 0 LJ | Day 14 UJ | Day 14 LJ | Day 28 UJ | Day 28 LJ |
|---|---|---|---|---|---|---|
| Delmopinol | | | | | | |
| 1 | 0 | 4 | 3 | 1 | 6 | 3 |
| 2 | 1 | 4 | 4 | 1 | 7 | 2 |
| 3 | 0 | 4 | 3 | 1 | 4 | 4 |
| 4 | 0 | 3 | 3 | 2 | 4 | 3 |
| Sum | 1 | 15 | 13 | 5 | 21 | 12 |
| Control | | | | | | |
| 1 | 0 | 4 | 10 | 2 | 6 | 4 |
| 2 | 0 | 4 | 9 | 2 | 8 | 3 |
| 3 | 1 | 4 | 7 | 1 | 3 | 4 |
| 4 | 0 | 4 | 10 | 3 | 9 | 3 |
| Sum | 1 | 16 | 36 | 8 | 26 | 14 |

TABLE 3

Number of teeth with calculus on the buccal surfaces of the teeth in of the upper jaw during the experimental period of 28 days (n = 48 measured sites).

| Dog | Day 0 | Day 14 | Day 28 |
|---|---|---|---|
| Delmopinol | | | |
| 1 | 0 | 2 | 8 |
| 2 | 0 | 4 | 12 |
| 3 | 0 | 0 | 7 |
| 4 | 0 | 0 | 10 |
| Sum | 0 | 6 | 37 |
| Control | | | |
| 1 | 0 | 10 | 11 |
| 2 | 0 | 10 | 12 |
| 3 | 0 | 12 | 12 |
| 4 | 0 | 3 | 5 |
| Sum | 0 | 35 | 40 |

The invention claimed is:

1. A composition comprising a morpholino compound having the formula (I), for use in the treatment of gingivitis and for concomitant treatment of halitosis in a companion animal

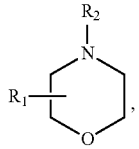

(I)

wherein R1 is a straight or branched alkyl group containing 8 to 16 carbon atoms at the 2- or 3-position of the morpholino ring, and R2 is a straight or branched alkyl group containing 2 to 10 carbon atoms, substituted with a hydroxy group except in the alpha-position, or a pharmaceutically acceptable salt thereof, the composition being coated onto or infused into an animal chew, wherein the composition is infused into the animal chew by soaking the animal chew in the compound of formula (I) and allowing the animal chew to dry.

2. A composition for use according to claim 1, wherein the sum of the carbon atoms in the groups R1 and R2 of the morpholino compound is at least 10.

3. A composition for use according to claim 1 or 2, wherein R2 terminates with the hydroxy group.

4. A composition for use according to claim 1, wherein the morpholino compound is 3-(4-propyl-heptyl)-4-(2-hydroxyethyl) morpholine.

5. A composition for use according to claim 1, wherein the animal is a dog.

6. A composition for use according to claim 1, wherein the animal is a cat.

7. A composition for use according to claim 1, further comprising a pharmaceutically acceptable excipient.

8. A composition for use according to any preceding claim 1, further comprising an anti-inflammatory agent.

9. The composition for use according to claim 2, wherein the sum of the carbon atoms in the groups R1 and R2 of the morpholino compound is between 10 and 20.

* * * * *

UNITED STATES PATENT AND TRADEMARK OFFICE
CERTIFICATE OF CORRECTION

PATENT NO. : 10,206,928 B2
APPLICATION NO. : 15/801109
DATED : February 19, 2019
INVENTOR(S) : Rolf Valter Attstrom et al.

It is certified that error appears in the above-identified patent and that said Letters Patent is hereby corrected as shown below:

On the Title Page

Item (73) "Merial Inc." should read --Merial Inc. and Maelor Laboratories Limited--

Signed and Sealed this
Twenty-ninth Day of November, 2022

Katherine Kelly Vidal
*Director of the United States Patent and Trademark Office*